(12) United States Patent
Srinivasan et al.

(10) Patent No.: US 12,702,290 B2
(45) Date of Patent: Aug. 11, 2026

(54) INTEGRATED APPARATUS FOR VISUAL FUNCTION TESTING AND METHOD THEREOF

(71) Applicant: Forus Health Pvt. Ltd., Bangalore (IN)

(72) Inventors: Venkatakrishnan Srinivasan, Bangalore (IN); Revathy Manthri Rangaraj, Bangalore (IN); Subhajit Banerjee Purnapatra, Bangalore (IN); Ranjith Kumar, Bangalore (IN); Keerthighaan Kanagasegar, Bangalore (IN)

(73) Assignee: Forus Health Pvt. Ltd., Bangalore (IN)

( * ) Notice: Subject to any disclaimer, the term of this patent is extended or adjusted under 35 U.S.C. 154(b) by 628 days.

(21) Appl. No.: 18/004,211

(22) PCT Filed: Sep. 7, 2021

(86) PCT No.: PCT/IN2021/050872
§ 371 (c)(1),
(2) Date: Jan. 4, 2023

(87) PCT Pub. No.: WO2022/074670
PCT Pub. Date: Apr. 14, 2022

(65) Prior Publication Data

US 2023/0255473 A1 Aug. 17, 2023

(30) Foreign Application Priority Data

Oct. 6, 2020 (IN) ............................ 202041043483

(51) Int. Cl.
*A61B 3/028* (2006.01)
*A61B 3/00* (2006.01)
*A61B 3/024* (2006.01)

(52) U.S. Cl.
CPC ............ *A61B 3/028* (2013.01); *A61B 3/0041* (2013.01); *A61B 3/024* (2013.01)

(58) Field of Classification Search
CPC ....... A61B 3/028; A61B 3/0041; A61B 3/024; G02B 2027/0185; G02B 27/0172;
(Continued)

(56) References Cited

U.S. PATENT DOCUMENTS 5,550,602 A 8/1996 Braeuning
5,864,384 A 1/1999 Mcclure et al.
(Continued)

FOREIGN PATENT DOCUMENTS

WO WO-2017113192 A1 * 7/2017 ......... G02B 27/0172
WO 2018163166 A2 9/2018

OTHER PUBLICATIONS

Hearing Notice issued in corresponding Indian Patent Application No. 202041043483 on Apr. 18, 2023.

*Primary Examiner* — William R Alexander
*Assistant Examiner* — Mackenzi Bourquine
(74) *Attorney, Agent, or Firm* — The Belles Group, P.C.

(57) ABSTRACT

This disclosure discloses an apparatus and method thereof for a comprehensive visual function testing apparatus. A plurality of visual test stimuli may be spatiotemporally sequenced and presented to the subject undergoing visual function tests including, but not limited to, visual acuity test, stereoscopic vision test, field of vision test and contrast sensitivity test. Furthermore, by combining all the elements under the same computational device, it streamlines the conventional visual function testing process, provides automated visual function testing of subjects, and refraction correction when required, such as for perimetry testing. Such an apparatus opens up unprecedented possibilities for refining the visual function testing process. High degree of
(Continued)

integration resulting from adoption of the features disclosed, a variety of compact, portable, wearable embodiments may be achieved.

10 Claims, 9 Drawing Sheets

(58) Field of Classification Search
CPC .......... G02B 27/017; G02B 2027/0178; G02B 27/0101; G02B 2027/014
USPC .......................................... 351/222, 206, 211
See application file for complete search history.

(56) References Cited

U.S. PATENT DOCUMENTS

| | | | | |
|---|---|---|---|---|
| 6,045,227 | A | 4/2000 | Stewart et al. | |
| 6,386,706 | B1 | 5/2002 | Mcclure et al. | |
| 2013/0127980 | A1* | 5/2013 | Haddick | G06F 3/013 348/14.08 |
| 2016/0026253 | A1* | 1/2016 | Bradski | H04N 13/128 345/8 |
| 2018/0116509 | A1 | 5/2018 | Myung et al. | |
| 2019/0004325 | A1* | 1/2019 | Connor | G02B 27/0172 |
| 2019/0391399 | A1 | 12/2019 | Samec et al. | |
| 2020/0008667 | A1* | 1/2020 | Raviv | A61B 3/0033 |

* cited by examiner

INTEGRATED APPARATUS FOR VISUAL FUNCTION TESTING AND METHOD THEREOF

CROSS-REFERENCE TO RELATED APPLICATION

The present application is a U.S. national stage application under 35 U.S.C. § 371 of PCT/IN2021/050872, filed Sep. 7, 2021, which claims priority to Indian patent application number 202041043483 filed on Oct. 6, 2020 The disclosures of the aforementioned priority applications are incorporated herein by reference.

FIELD OF INVENTION

This disclosure belongs to the field of medical ophthalmic apparatus and methods thereof for testing visual function of subjects.

BACKGROUND OF INVENTION

Testing visual function involves performing one or more tests for assessing various aspects of a subject's vision. Some of these tests are as follows. Visual acuity test, in which errors in refraction in a subject's vision are measured. These measurements are used for correcting the subject's vision with prescription eyewear. Visual field test or perimetry, which spatially maps a subject's field of vision and identifies irregularities in the mapped field, thereby identifying certain conditions. These could be macular degeneration or glaucoma induced damaged optic nerve, for example.

There are well established procedures for such visual function tests and are well known in the art. For example, visual acuity is conventionally tested by positioning standard vision charts, such as a Snellen chart, at a specified distance from the subject and asking the subject to identify the letters or symbols on the chart. Commonly, the distance is six meters. This test is used to assess the subject's vision with and without refraction error correction. Conventional visual field testing, on the other hand, employs a perimetry apparatus, such as the Humphrey field analyzer. The analyzer comprises a hemispherical cavity, on the inner wall of which, visual stimulus is flashed at different positions and with unequal time gaps between flashes. The subject has to look at the inner wall and has to respond, by pressing a pushbutton for example, every time a flash is perceived. The subject's responses are recorded. The results are analyzed to determine the field of vision. The positions at which there was a visual stimulus but, the subject did not perceive it, indicates the limitations of the subject's field of vision. For example, a subject with macular degeneration will be incapable of perceiving the stimuli at the very center of the field of vision.

Those well versed in the art are familiar with some of the limitations of these conventional test methods and apparatus. One such limitation common to most of these is space. For instance, standard visual acuity testing needs six meters of distance between the subject and the chart. This is often reduced to three meters using a mirror that reflects a chart placed near the subject so that the perceived distance is six meters. It is also necessary for the chart to be positioned stably. State-of-the art perimetry apparatus, such as the Humphrey field analyzer, is bulky and hence, restricted for use, mostly, in clinical environments, often specialized or dedicated ones.

Further, conventional visual function test apparatuses are configured for only one test and each apparatus is employed to assess one specific aspect of a subject's vision. This necessitates investment on and procurement, installation, and maintenance of multiple apparatuses. This may make such facilities expensive to establish, operate, and maintain. This may also make the use of such facilities expensive for the subjects.

The need for multiple apparatuses also complicates the process of testing or assessment. For example, if the subject has high refraction error it is known to significantly affect the results of the perimetry test, indicating a less than actual field of vision of the subject. This has been well established by various studies. Thus, refraction error should be corrected before evaluating field of vision. Such correction would first require a refraction test and subsequent correction, such as prescription glasses or trial lenses. Once the subject has procured them or fitted with them, field of vision may be assessed. Thus, the entire process may not be completed during a single visit by the subject to a facility and may involve multiple visits, and the use of multiple apparatuses.

A number of methods and apparatuses have been disclosed to address some of the problems mentioned above. Most notably, virtual reality based compact systems are disclosed such as the one in the exemplary patents mentioned below.

U.S. Pat. No. 5,864,384 A describes a head-mounted virtual reality environment capable of presenting computer driven, sequenced test stimuli with bi-directional interaction between subject and a computer. This patent teaches general tests such as visual field performance, visual acuity, and color vision with particular focus on visual field evaluation, utilizing a virtual reality setup for portability and reduced subject fatigue.

U.S. Pat. No. 6,386,706 B1 describes a similar setup incorporating a virtual retinal display system along with integration of telemedicine techniques for centralized diagnostic interpretation of visual field tests performed at remote locations. The aforementioned patent also identifies and addresses challenges related to bulkiness of conventional visual perimetry apparatus.

A solution is suggested in U.S. Pat. No. 6,045,227 A, which claims to achieve multi-function visual function testing with a single apparatus comprised of computer controlled close proximity display units and associated viewing optics.

The U.S. Pat. No. 5,550,602 A also teaches a compact spectacle or helmet type wearable system with integrated displays for computer controlled visual stimulus presentation for general visual function testing.

None of them, however, attempt to solve all the problems in the state-of-the-art apparatus described above, such as, a simple head mounted device for conducting comprehensive visual tests, including subjective refraction solving the problem of space required to install the various equipment needed for multiple equipment, cost of the equipment and other associated problems. Additionally the U.S. Pat. No. 5,550,602 suffers from the drawback that the adjustments of the position of, what the patent refers to as, "pertaining field lens 27" has to be displaced to either manually or electrically to correct for the refraction errors in the subject's vision. This makes the operation of the device cumbersome, prone to errors, and may need skill to operate.

SUMMARY OF INVENTION

Thus, there is a need for an apparatus and a method that can overcome at least one of the drawbacks mentioned above in the presently known apparatus and methods. Thus, the primary object of the disclosed apparatus and method is to provide a portable apparatus for comprehensive vision testing. Further, it is an object of the present disclosure to provide an apparatus that obviates the need for a large space, as hitherto required, for example the six-meter distance between the subject and the chart. It is a further object of the disclosed method and apparatus to enable a combined visual function testing apparatus and method.

The present disclosure discloses an apparatus comprising variable optics sub-systems using a tunable lens per eye of the subject for refraction error correction and compensation and an integrated visual stimulus generator housed in an enclosure and controlled by a computational device. This provides visual function testing that streamlines the clinician's workflow. Embodiments may also aid or achieve automated testing.

This disclosure discloses an apparatus comprising the following. The apparatus is wearable by the subject under test, in which, the subject looks at the visual stimulus through the tunable lens optics sub-system. The visual stimulus, for example a Snellen chart, is displayed on a display integral to the head mounted apparatus. The subject responds to the stimuli and the responses are fed back to the computational device. Based on the subject's responses, the tunable lens is controlled by the computational device until the refraction error in the subject's vision is corrected. It must be noted here that even though there may be a tunable lens for each eye, the description may often refer to a single tunable lens. However, it must be assumed that the description that applies to one lens, applies to the other lens also.

Thus, disclosed is an apparatus for conducting one or more tests of a subject's vision, wherein the apparatus is configured for being worn by the subject, the apparatus comprises a display device for displaying a visual stimulus, a feedback unit for receiving a response of the subject to the visual stimulus and conveying it to a computational device, a tunable lens; and the computational device configured for controlling the display device for displaying the visual stimulus to the subject for the subject to view through the tunable lens, determining one or more characteristics of the vision of the subject based on the subject's response conveyed through the feedback unit, tuning the characteristics of the tunable lens based on the determined one or more characteristics, and outputting the values of the determined one or more characteristics of the vision of the subject.

In one implementation an independent unit for conducting objective refraction testing is attached to the head mounted device described above. This unit projects a pattern into the eye of the subject wearing the head mounted unit and the image of the pattern formed on the subjects retina is captured by an electronic screen such as the one in a digital camera, a Charge Coupled Device, for example. Based on the image captured by the electronic screen, the computational device determines the refraction error of the subject's vision. The computational device then sets the characteristics of the tunable lens to compensate for the refraction errors in the subject's vision. During the further tests, the subject views the stimulus displayed by the display device and this may be used as the starting point of all further tests for determining the characteristics of the subject's vision.

Also disclosed is a method for conducting one or more tests of a subject's vision, wherein the subject is wearing an apparatus configured for being worn by the subject, the method comprising the steps of displaying a first visual stimulus to the subject on a display device the display device being controlled by a computational device configured for controlling the display on the display device, for sensing an image formed on the retina of the subject's eye by an electronic screen, measuring the refraction error of the subject's vision based on the image sensed by the electronic screen the computational device, compensating for the measured refraction error of the subject's vision by a tunable lens when the subject views the visual stimulus through the tunable lens, energizing electrodes of the tunable lens for altering one or more characteristics of the tunable lens, by the computational device based on the measured error, displaying a second visual stimulus on the display device, by the computational device, for viewing through the tunable lens by the subject, conveying the subject's response to the second visual stimulus, by a feedback unit configured for receiving the subject's response to the second visual stimulus, to the computational device wherein the computational device is configured for determining one or more characteristics of the vision of the subject, and outputting the values of the refraction error and one or more characteristics of the subject's vision.

The summary above is illustrative only and is not intended to be in any way limiting. Further aspects, exemplary embodiments, and features will become apparent by reference to the drawings and the following detailed description.

BRIEF DESCRIPTION OF DRAWINGS

These and other features, aspects, and advantages of the exemplary embodiments can be better understood when the following detailed description is read with reference to the accompanying drawings in which like characters represent like parts throughout the drawings, wherein.

Figure 1:
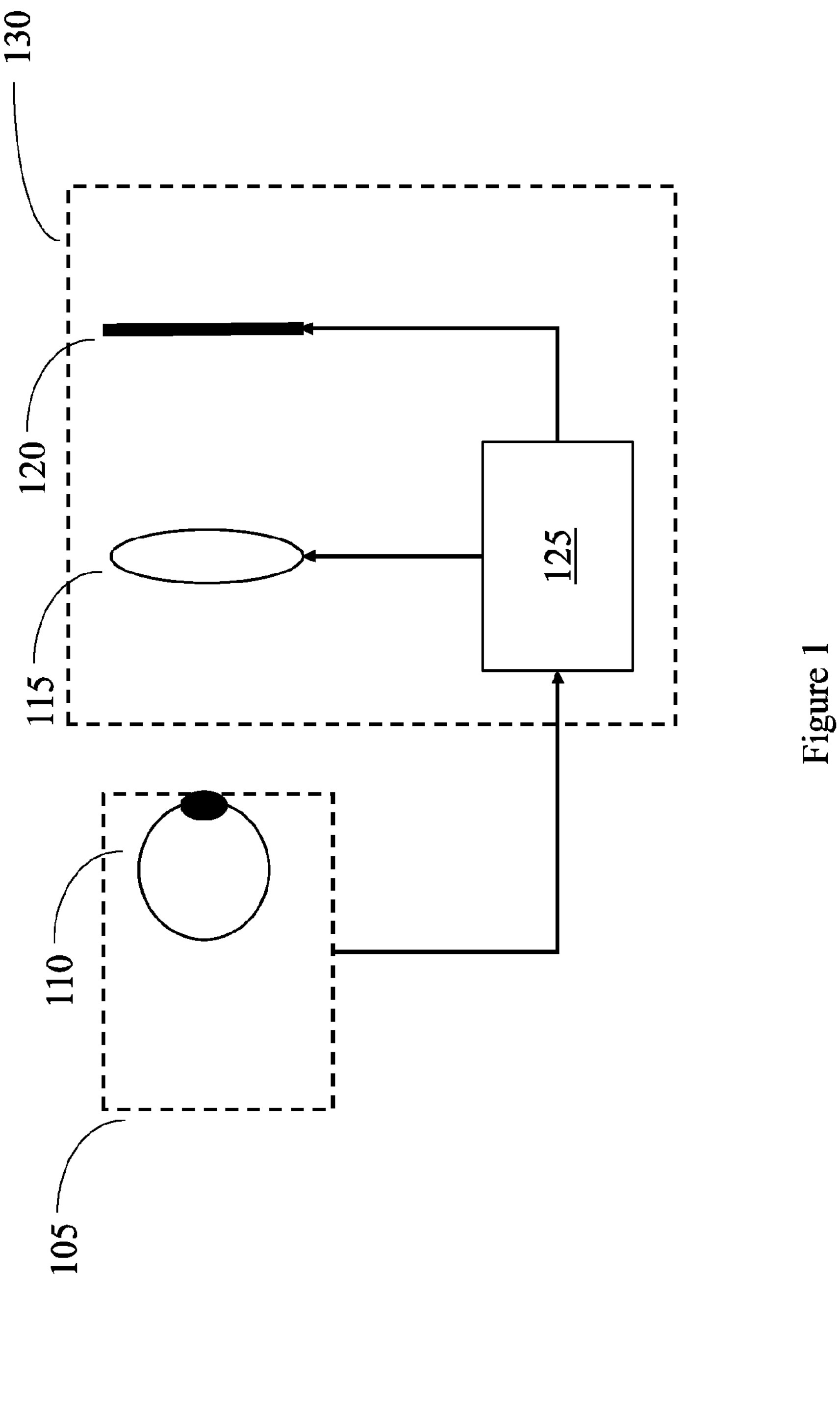
FIG. 1 shows a simplified diagram of one aspect of the disclosed apparatus used for testing the subject's eyes for refraction.

Further, skilled artisans will appreciate that elements in the figures are illustrated for simplicity and may not have necessarily been drawn to scale. Furthermore, in terms of the construction of the device, one or more components of the device may have been represented in the figures by conventional symbols, and the figures may show only those specific details that are pertinent to understanding the embodiments of the present invention so as not to obscure the figures with details that will be readily apparent to those of ordinary skill in the art having the benefit of the description herein.

DETAILED DESCRIPTION

For the purpose of promoting an understanding of the principles of the invention, reference will now be made to the embodiments illustrated in the figures and specific language will be used to describe the same. It will nevertheless be understood that no limitation of the scope of the invention is thereby intended, such alterations and further modifications in the illustrated system, and such further applications of the principles of the invention as illustrated therein being contemplated as would normally occur to one skilled in the art to which the invention relates.

It will be understood by those skilled in the art that the foregoing general description and the following detailed description are exemplary and explanatory of the invention and are not intended to be restrictive thereof.

The terms "comprises", "comprising", or any other variations thereof, are intended to cover a non-exclusive inclusion, such that a process or method that comprises a list of steps does not comprise only those steps but may comprise other steps not expressly listed or inherent to such process or method. Similarly, one or more apparatus or sub-systems or elements or structures or components proceeded by "comprises . . . a" does not, without more constraints, preclude the existence of other apparatus or other sub-systems or other elements or other structures or other components or additional device apparatus or additional sub-systems or additional elements or additional structures or additional components. Appearances of the phrase "in an embodiment", "in another embodiment" and similar language throughout this specification may, but do not necessarily, all refer to the same embodiment.

Unless otherwise defined, all technical and scientific terms used herein have the same meaning as commonly understood by one of ordinary skill in the art to which this invention belongs. The system, methods, and examples provided herein are illustrative only and not intended to be limiting.

In some embodiments, the word 'patient', 'subject', and 'user' used in the description may reflect the same meaning and may be used interchangeably. The terms user, operator, optometrist, and ophthalmologist may also be used interchangeably and refers to a person who has taken up the task of testing the subject's vision.

In addition to the illustrative aspects, exemplary embodiments, and features described above, further aspects, exemplary embodiments of the present disclosure will become apparent by reference to the drawings and the following detailed description.

FIG. 1 is a simplified diagram illustrating the principle of testing an eye 110 of a subject 105, with the disclosed apparatus 100. The subject 105 views a visual stimulus 120, a Snellen chart, for example, through a tunable lens 115. The power of the tunable lens 115 is set, however, to 0 (zero) diopter and hence does not alter the vision of the subject 105. Based on the feedback from the subject 105, the power of the tunable lens 115 is changed appropriately by the computational device 125 such that the vision of the subject 105 is defect free or nearly defect free while the subject 105 views through the tunable lens.

Figure 2:
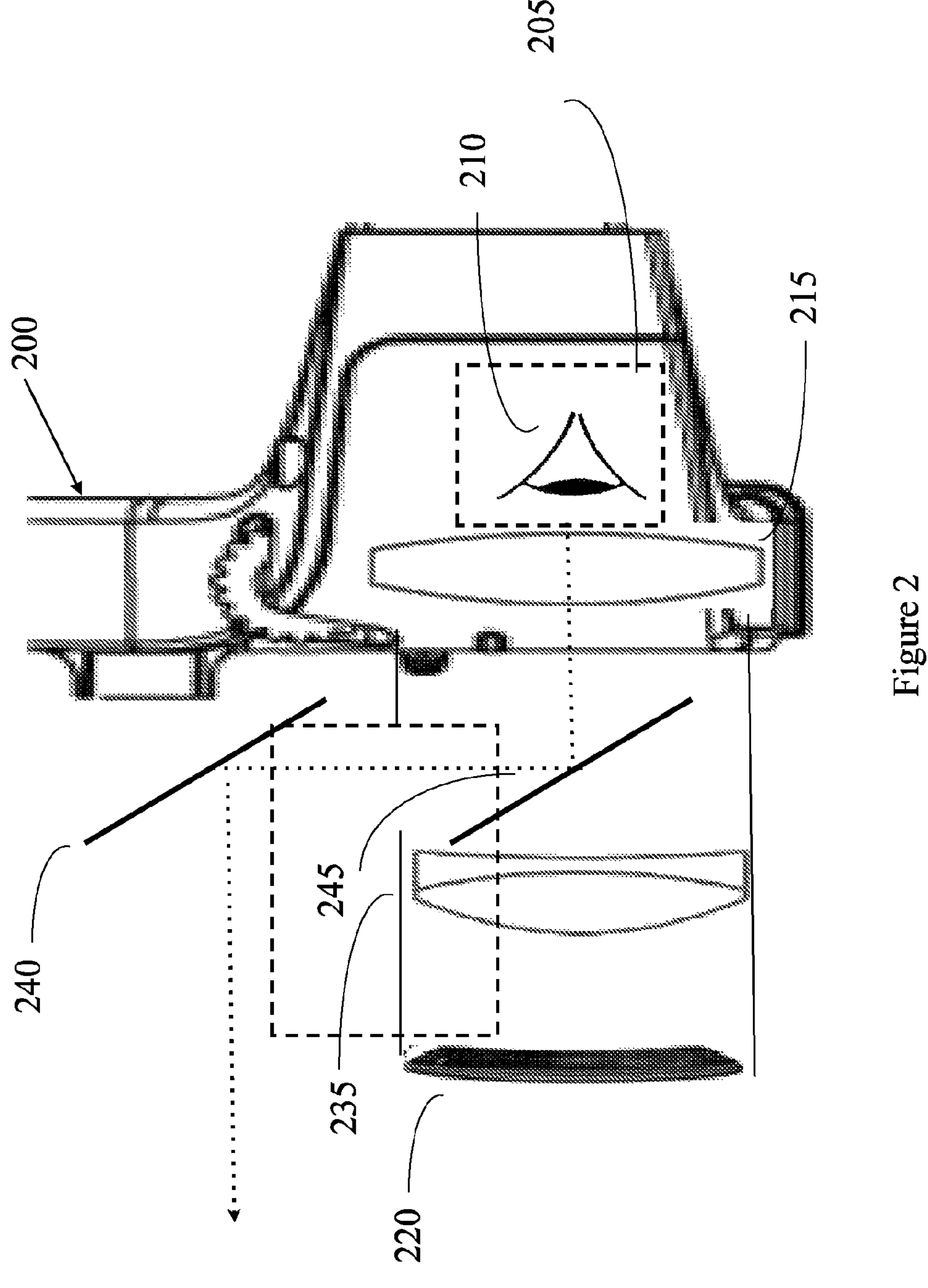
FIG. 2 shows a simplified exemplary embodiment of the disclosed apparatus configured for testing the subject's vision in a form adopted for adjustments by an operator.

The disclosed apparatus 100 may have a plurality of embodiments, one of them being diagrammatically shown in FIG. 2. For example, the apparatus 100 may have an integrated digital display 220 with the optics sub-system 235 for presenting visual stimuli at a fixed distance from the eye 210 of the subject 205. In another embodiment it may have an integrated digital projector (not shown) with the optics sub-system 235 for projecting visual stimuli at an arbitrary distance. The apparatus 200 may have visual stimuli such as Snellen chart, LogMAR chart, tumbling E chart, astigmatic fan chart, duochrome chart, oculo-kinetic visual field test chart, equivalent of Amsler grid, etc. that may be chosen by the operator or the subject 205. The operator may perform one or more visual function tests depending on the subject's requirement or as prescribed by an ophthalmologist.

Subjective refraction may be defined, in a simple way, as an attempt to determine, by trial and error using the patient's cooperation, the combination of lenses that will provide the best corrected visual acuity. Objective refraction may be defined as a refraction measurement obtained without receiving any feedback from the patient, using a retinoscope or auto-refractor. For example, if subjective refraction tests need to be done, objective refraction measurement may be conducted first, perhaps using an integrated device or a separate one, configured for conducting such a test. The user may then use the values so obtained as a starting point for setting the characteristics of the tunable lens for conducting subjective refraction tests. This may also save the time taken for subjective refraction test with an arbitrary value for compensating for the refraction error in the subject's vision as a starting point.

The process of using the disclosed apparatus 200 will be described now. The disclosed apparatus 200 must be setup for the individual subject. For example, as the apparatus 200 is a wearable one, as shown in FIG. 2, the process starts with fitting the apparatus 200 on the subject 205, on the subject's head for instance, and aligning the centers of the tunable lens 215 to the subject's inter-pupillary distance (not shown). As is well known, the distance between the pupils of the eyes are different for different subjects. The apparatus 200 has to be set for each subject such that the visual stimuli are presented directly in front of the pupil of each eye, as well. The visual stimulus will be set to relevant chart on the digital display 220, for subjective refraction. Adhering to conventional subjective refraction processes, monocular testing, binocular balancing, and binocular refraction of the subject's vision may be performed with the apparatus 200. Near vision test, for measuring the refraction error while the subject is reading, such as reading a book, may also be performed, if required, by controlling the positions of the optics sub-system 235.

Furthermore, as shown in FIG. 2, a retractable periscopic arm, mirrors 240, 245 enable an operator to view the subject's eyes and adjust the inter-pupillary distance. Even though half mirrors are shown in FIG. 2 the optics sub-system 235 may be realized with of a suitable functional combination of full or half mirrors, beam splitters and prisms. The tunable lens 215 is de-energized or suitably energized to have 0 diopter power, depending on the characteristics of the tunable lens, to view the subject's eye 210 through the tunable lens 215. After adjusting for the inter-pupillary distance, the tunable lens 215 is set to be co-axially aligned with the eyes 210 of the subject. The adjustment mechanism may be configured through mechanical or electro-mechanical means (not shown).

The digital display 220 is communicatively connected to the computational device 125 either through a wired or wireless connection (not shown). For the sake of simplicity, the computational device is not shown in FIG. 2 and FIG. 3 and hence referred to here with reference to FIG. 1. The computational device 125 drives the digital display 220 to render visual stimuli and controls the diopter power of the tunable lens 215. Therefore, both the visual stimuli and the diopters may be changed simultaneously based on the feedback from the subject or operator, for arriving at the correct prescription glasses during subjective refraction measurement. Once the refraction measurement is completed, other tests of vision may be performed. In cases where the subject's vision has refraction errors, previously computed visual acuity compensation is applied through the tunable lens 215 prior to performing other tests.

Figure 3:
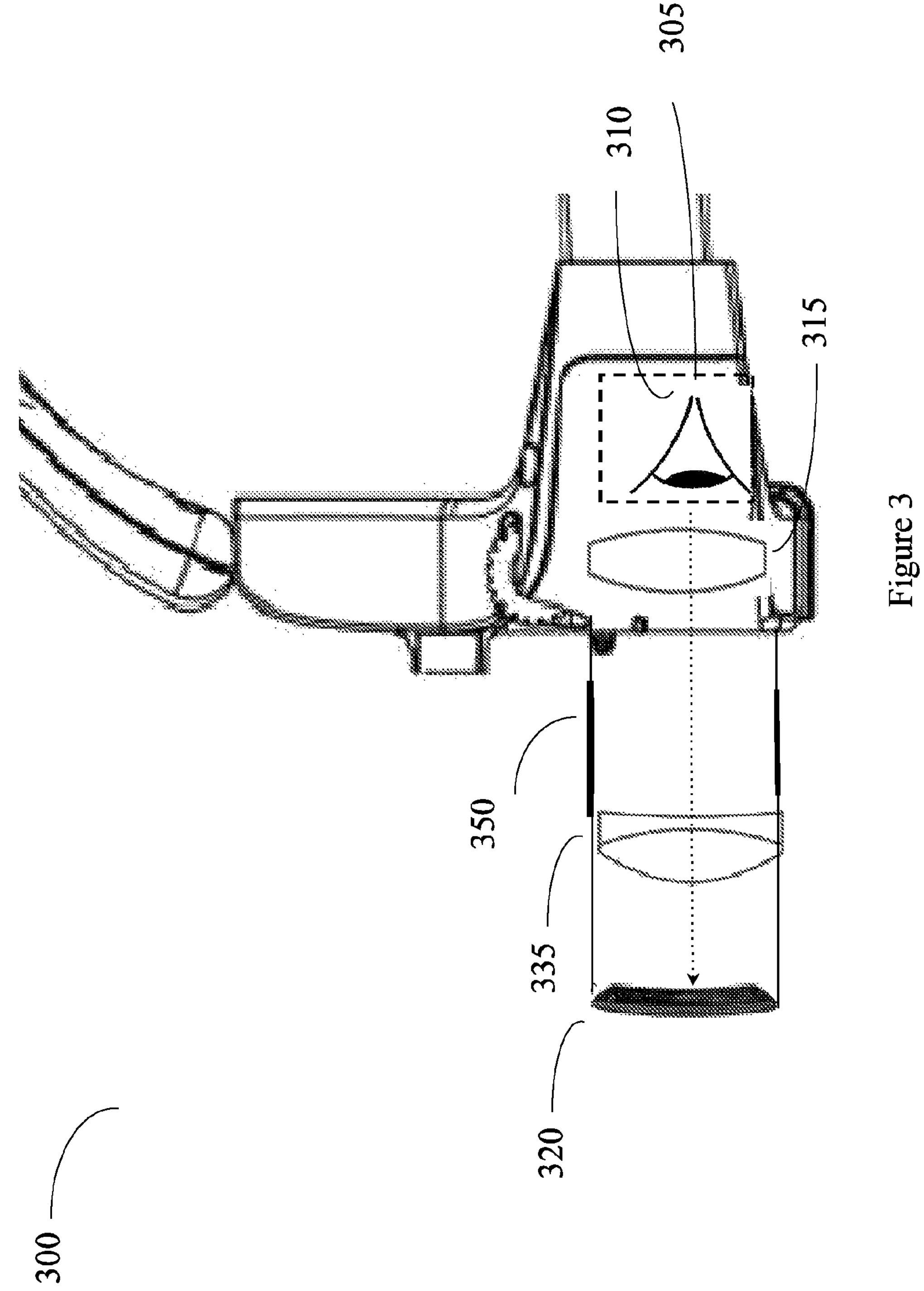
FIG. 3 shows an exemplary, head mounted embodiment of the disclosed apparatus configured for testing the subject's vision while in use for testing the subject's vision for refraction errors.

After subjective refraction test is complete, other visual function tests such as visual field test may be performed. Because the subjective refraction and visual field test are conducted with the same apparatus, the measured refraction error may be compensated for by tuning the tunable lens 315 before conducting visual field test as shown in FIG. 3. A systematic measurement of visual field function may be performed by then projecting test stimuli on a fixed background. The visual stimulus is presented to the subject 305 on the digital display 320 at different time intervals, luminous intensities and at different locations in the field of vision. Feedback from the subject 305 is captured by the feedback unit (not shown in figure) and conveyed to the computational device 125. It is to be noted that the feedback here refers to the subject 305 indicating by any predefined means that the subject 305 has perceived the visual stimulus such as by pressing pushbutton. Alternatively, vocalized responses could also be used by appropriate arrangements.

Depending on the type of visual stimulus chosen, a plurality of tests may be conducted. Examples of such tests are macular function assessment, differential light sensitivity at the periphery of the visual field, etc. As is known, here, macula refers to the small central area of the retina of the eye that controls visual acuity. In many subjects, especially with age, the sensitivity of the macula degenerates and it is important to test macular function. Subjects with refraction errors would have their refraction error compensated for, by applying the corrections through the tunable lens, prior to visual field testing to significantly improve accuracy of perimetry tests.

In a similar fashion, other visual function tests such as tests of color vision, contrast sensitivity, etc., may also be performed. Furthermore, the integration of these visual function testing mechanisms with a tunable lens based in a single apparatus, disclosed in the present disclosure, enhances clinical efficiency. Instead of moving from apparatus to apparatus, an entire range of visual function tests may be conducted with a single apparatus. Advantageously all these tests may be conducted during a single visit of the subject to the facility and even in a single sitting.

Continuing with reference to FIG. 3, in one embodiment, the disclosed apparatus 300 may comprise tunable lens 315, an integrated digital display 320 and an optics sub-system 335. The digital display 320 may be one of the known technologies, OLED or backlit LCD and so on, for example. The optics sub-system 335 may be of a doublet lens configured to make the display perceived to be at infinity even though it is close to the subject's eyes. As is well known, a doublet is a type of lens made up of two simple lenses paired together. Such an arrangement allows more optical surfaces, thicknesses, and formulations, especially as the space between lenses may also be considered an element. The digital display 320 acts as the means of presenting the visual stimuli. Along with the aforementioned setup is an electrically tunable lens 315 for each eye, which may be controlled to change its spherical and astigmatic diopter and angle, intended for testing and compensating for the subject's refraction error. For simplicity's sake only one eye is shown in FIG. 3.

Whereas in one implementation the tunable lenses are controlled by applying suitable electrical voltages to the electrodes of the tunable lenses. Tunable lenses, however, whose characteristics may be controlled by mechanical stress may also be used. PDMS-made lenses (lenses made using Polydimethylsiloxane) is one such example. The use of such other possible tunable lenses that are controlled by other variables are also within the scope of this disclosure. In the interest of brevity and ease of understanding, in the description hereinafter, reference may only be made to the application of suitable electrical voltages to the electrodes of the tunable lens. It must be understood that mutatis mutandis, such references apply to all other types of tunable lenses that may be available.

As shown in FIG. 3, during subjective refraction, the periscopic arm is retracted. The path between the digital display 320 and the subject's eye 310 may be protected from stray light entering the path with a suitable lid 350. During refraction error measurement, the vision chart is rendered on the electronic display 320.

Figure 4:
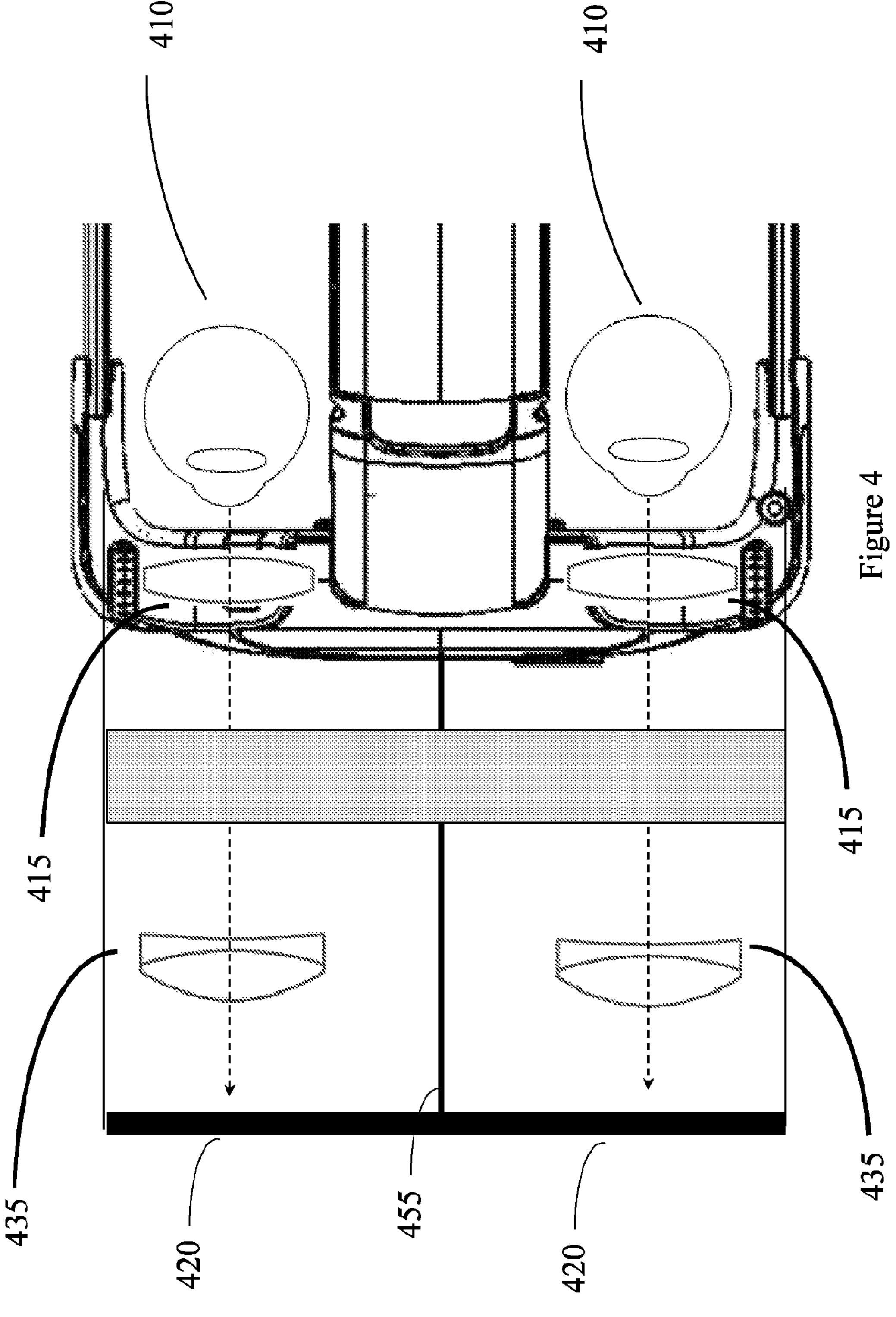
FIG. 4 is diagrammatic to view of the disclosed apparatus with integrated digital display.

FIG. 4 depicts the top view of the disclosed system, with the periscopic arm retracted. Each eye 410 is shown to be looking through a tunable lens 415 at the electronic display 420. An opaque divider 455 is provided between the eyes from near the eye till the display 420, to ensure that each eye 410 is looking straight ahead and not at the display meant for the other eye. This may be done for limiting optical decentering between the subject's eye and optics sub-system 435.

Figure 5:
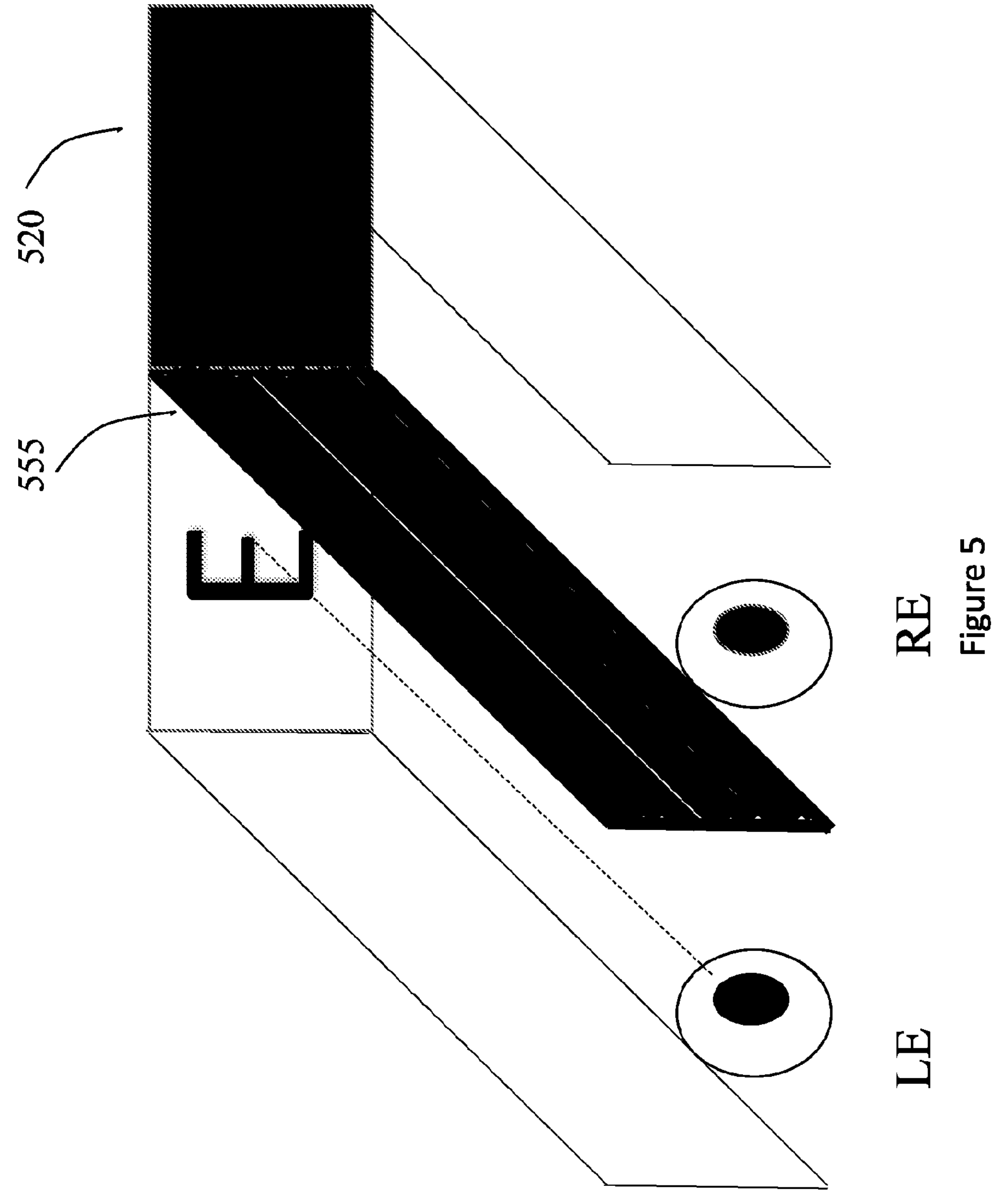
FIG. 5 is a diagrammatic view showing monocular vision testing.

During the monocular testing phase of subjective refraction, instead of occluding the eye not being tested, the digital display 520 in front of the eye to be occluded may be made dark by the computational device 125 for the same effect, as shown in FIG. 5 wherein the right eye, shown as RE, is to be occluded and hence the digital display 520 in front of the right eye RE is darkened.

Figure 6:
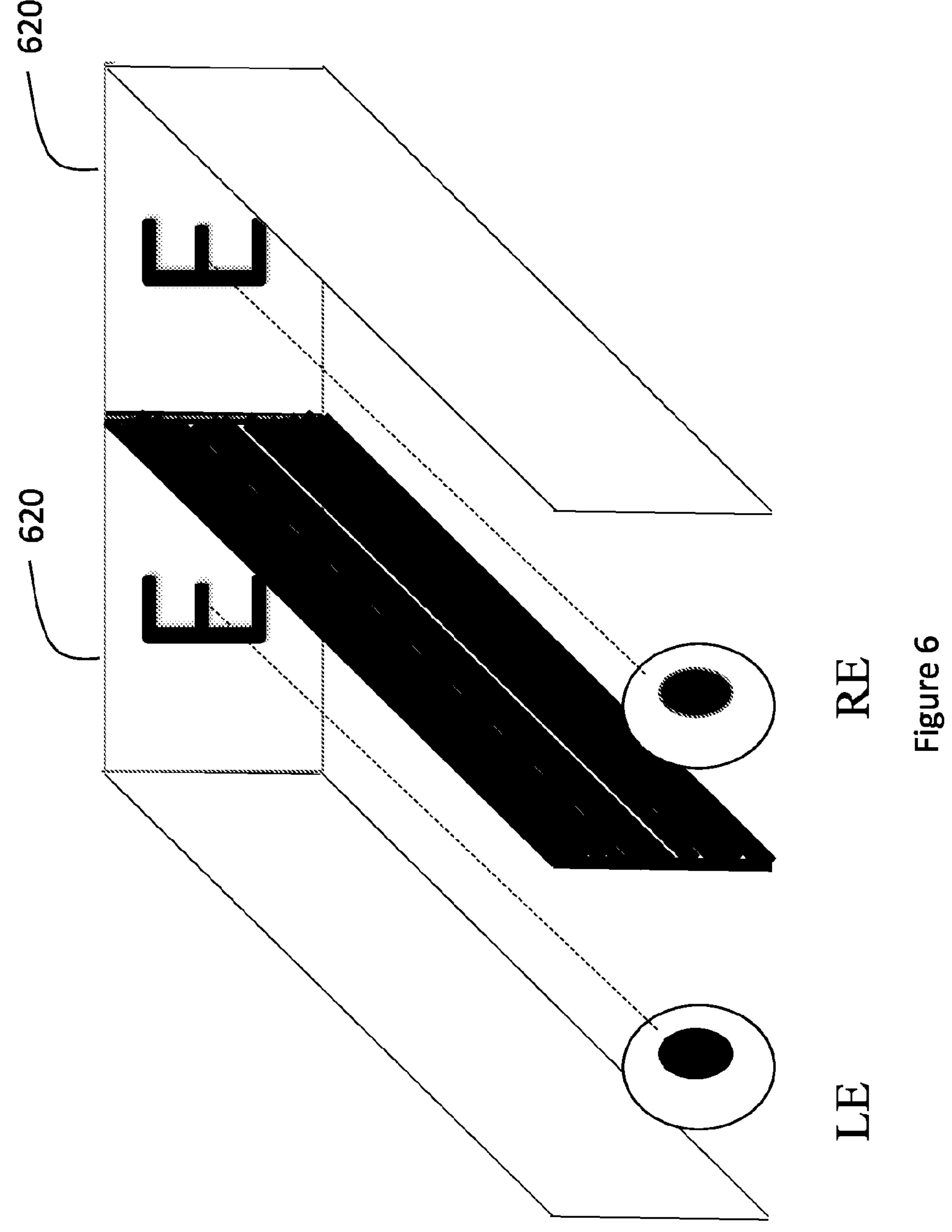
FIG. 6 is a diagrammatic view showing binocular vision testing.

FIG. 6 shows binocular testing for which neither eye is occluded and both portions of the digital display 620 will display the visual stimulus. Depending on the desired binocular stereoscopic output, the images rendered on each portion may be laterally shifted appropriately such that the subject perceives a single fused image as in the case of stereoscopic vision. For testing the other vision functions, the digital display 620 may be altered appropriately. For example, to perform perimetry, the setup in FIG. 5 may be used to test each eye independently, and spots of light flashes may be rendered instead of Snellen letters, for example.

Figure 7:
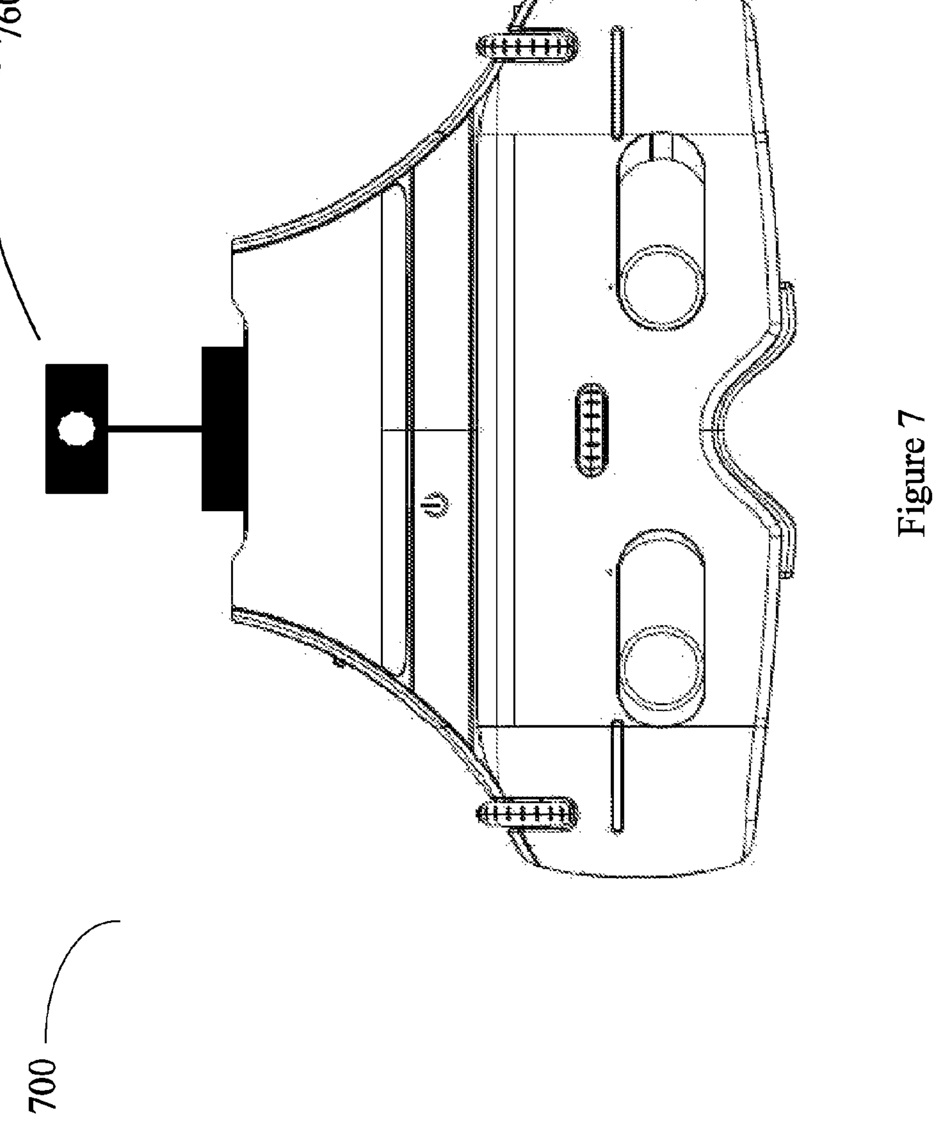
FIG. 7 shows the elevation of an embodiment of the disclosed apparatus comprising an integrated projector.

Another embodiment of the apparatus 700 disclosed herein comprises a projector 760, as shown in FIG. 7. Projector 760, as is known, is a device that projects images on a screen. The projector 760 is configured for projecting a visual stimulus on a passive screen, for the subject to see and read or recognize and is controlled by the computational device 125. The projection surface, for example a passive screen or a wall of suitable reflectivity and color, may be at a distance other than the recommended distance for a Snellen chart, that is, six meters. When the visual stimulus is displayed at a distance less than six meters, the size of the visual stimulus must be correspondingly smaller. To enable this, the disclosed apparatus comprises a proximity sensor (not shown) in communication with the computational device 125, 825 (Reference made to FIG. 1 and FIG. 8). The computational device 125, 825 calculates the distance between the subject and the passive screen based on one or more signals from the proximity sensor. The measured distance is then used to calculate the size of the visual stimulus to be projected on the passive screen and the projector is controlled by the computational device 125, 825 to display the visual stimulus having the calculated size.

Figure 8:
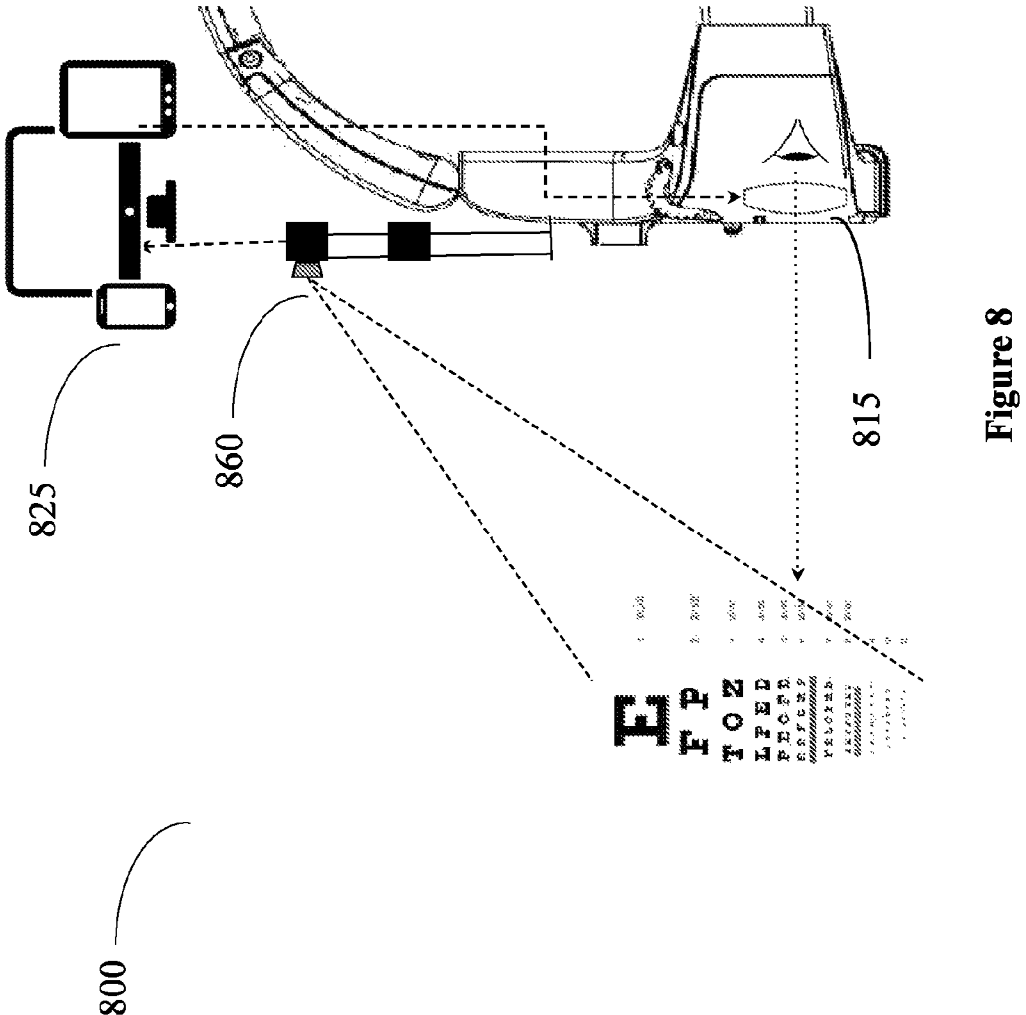
FIG. 8 shows another view of exemplary embodiment of the disclosed apparatus integrated projector projecting a chart at an appropriate distance.

As shown in FIG. 8 the projector 860 is integral to the disclosed device 800, in one embodiment, such that the visual stimulus is projected on to the passive screen, orthogonal to the optic axis. A computational device 825 controls the projector 860 and also controls the diopter power of the tunable lens. The visual stimulus may be projected in front of subject based on the visual stimulus chosen using the computational device 825 by an operator, for example an optometrist.

The projector 860 is positioned such that it does not interfere with the optical path of tunable lenses 815. In an operator operated mode, the operator has a view of the visual stimulus on the computational device 825 which is projected in front of the subject on the passive screen. The operator may select from the computational device 825 and project any pattern based on the test being performed.

The distance between projector 860 and the projection surface, that is, the passive screen is determined continuously using the proximity sensors. The optotype (Optotypes are usually letters, numbers, or geometric symbols. Each row of the chart used for visual acuity tests depicts optotypes of a different sizes) size for each line of visual acuity is then calculated based on the measured distance. Similarly, the visual stimulus for visual field testing may be adjusted, such as changing light intensity. If the distance between the projection subsystem and projection surface goes outside the applicable range, for example because of subject movement, the projection may be automatically paused and resumed after the subject resumes the original position.

Further, the disclosed apparatus may also have one or more light sensor modules in communication with the computational device. A first light sensor may be configured for measuring the ambient light around the subject. A second light sensor may be configured for measuring the ambient light on the passive screen, before a visual stimulus is projected thereon. Based on the signals from the light sensor, the computational device measures the ambient light or the ambient light on the passive screen. Based on these measured values, the brightness of the visual stimulus may be adjusted such that it is suitable for conducting the required tests. The second light sensor may also be configured for monitoring the brightness of the passive screen continuously with the projector projecting the visual stimulus to ensure that the visual stimulus continues to be at the calculated brightness.

Measurement of the ambient light on the passive screen is of particular importance while carrying out the field of vision test because, if the flash is not of sufficient brightness compared to the ambient brightness of the passive screen, even a person with unimpaired field of vision may miss the visual stimulus and hence lead to an inaccurate result. These measurements and control are carried out since it is known that the pupil of the eye contracts or dilates depending on the average brightness in the field of vision. The size of the pupil also influences the sharpness with which a scene is perceived by the eye.

The disclosed method of testing of the vision of a subject is now described. Described in brief, the method is as follows. Providing a visual stimulus to the subject on a display device, measuring the refraction error in the vision of the subject, compensating for the errors in the subject's vision, by controlling the characteristics of a tunable lens, when the subject views the visual stimulus through the tunable lens, receiving the subject's response to the visual stimulus and processing the response to output one or more values of the characteristics of the subject's vision.

Figure 9:
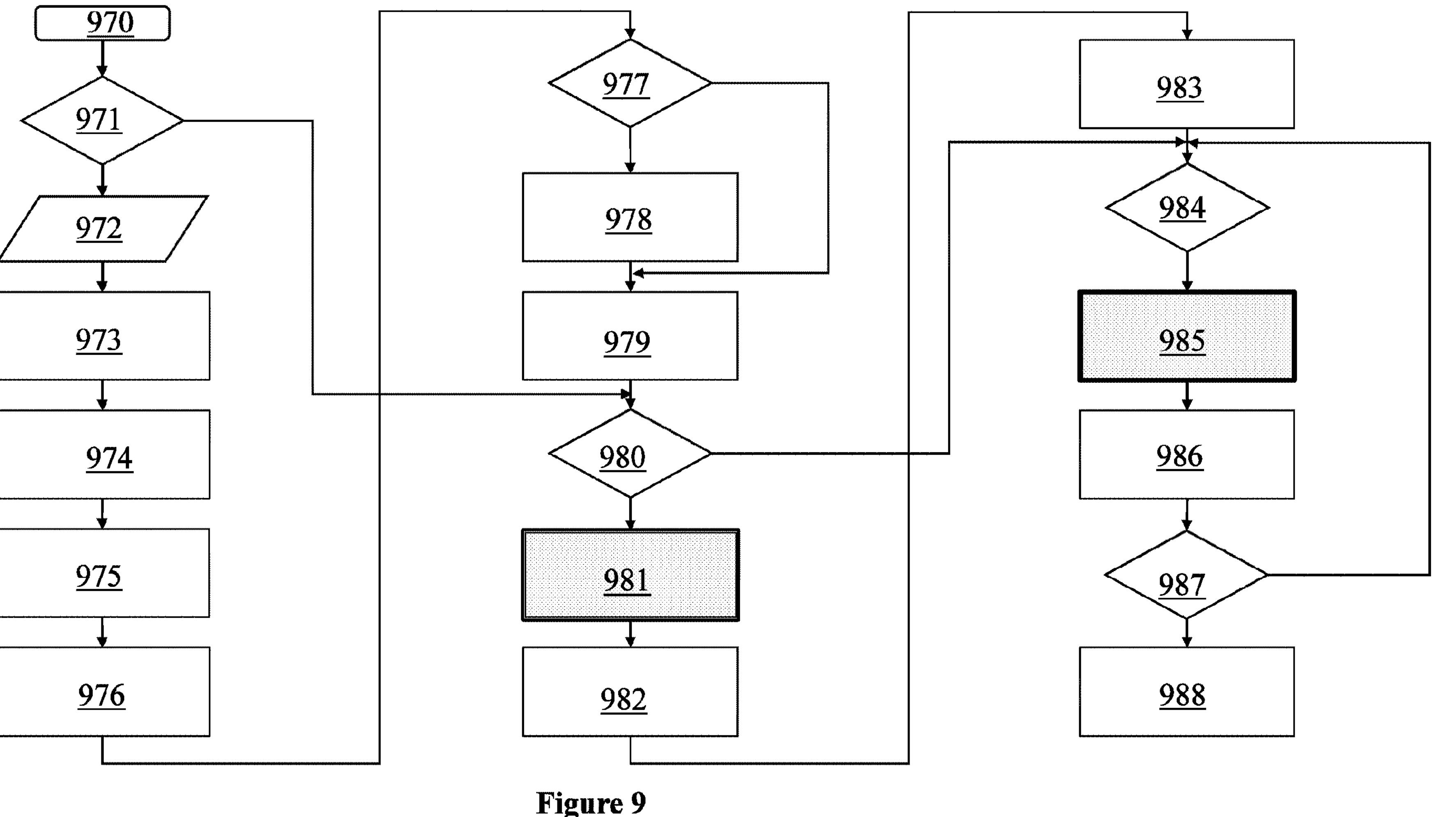
FIG. 9 shows a flow chart of the process of testing the vision of a subject with the disclosed apparatus.

An exemplary workflow that may be achieved by deploying the disclosed device is shown in FIG. 9. This also forms an elaboration of the disclosed method of testing a subject's vision. From FIG. 9 and the description that follows it can be seen that tests for refraction, correcting the errors in refraction, field of vision and color vision tests and other tests may be carried out at a single sitting and setup of the disclosed device.

The workflow begins at 970. At step 971 a decision is made by a user whether to start with refraction testing or proceed to the next test. If refraction test is not needed the flow moves to step 980 where a decision is made if a field of vision test is to be carried out or not. If field of vision tests is not needed, the flow continues to decision step 984. At decision 984, the test or tests to be carried out are determined and carried out in the subsequent steps.

Returning to step 971, if the decision is to conduct refraction testing, at step 972 the apparatus is set up for inter pupillary distance and other adjustments. At step 973 results of objective refraction tests conducted separately, beforehand, may be acquired, if available. When these values are input to the system, at step 974 the required visual stimulus, for example a Snellen chart, is displayed. At step 975, monocular refraction of each eye is conducted, that is, each eye of the subject is tested individually. That is, the digital display for one eye is a darkened digital display and the other digital display displays the visual stimulus for the other eye. Once the refraction error values for one eye is acquired, the other eye is tested. During that test the digital display associated with eye that was tested first is presented a darkened digital display and the digital display associated with the second eye displays the visual stimulus. When both eyes have been thus tested individually, binocular balancing is carried out in step 976. This is done because a person's vision is a combination of the visions of both eyes and hence the values of errors obtained first may have to be modified so that the vision of the subject can be corrected accurately with the modified values.

Next at step 977 a decision is made whether a near vision test is needed or not. This depends on the type of refraction error the subject has. This decision is made by the user, say an optometrist or ophthalmologist. If the decision is to conduct near vision tests it will be conducted at step 978 and the results of the test are combined with the results of the results from the step 976 in step 979.

At step 980, the user decides whether a field of vision test is needed or not. If it is needed, the errors in the vision of the subject or compensated for using the tunable lenses at step 981. At step 982 the visual stimulus for conducting the field of vision tests are set to conduct the tests and the test is conducted at step 983. If the decision, however, is that the field of vision test is not needed, the flow moves to 984 where the user decides if other tests are needed. If the decision is that no more tests are needed, the results of the tests until then are output for the user.

If the decision at 984 is further tests are needed, color vision test for example, at step 986 the tunable lenses are set to compensate for the errors in refraction. This may already have been done at step 981 but repeated here in case the flow moved directly to step 985 from step 971. The additional tests are then conducted. At the next step the user decides if any other tests are needed. If the decision is that more tests are needed the flow moves back to step 984. The flow between 987 and 984 may be repeated as many times as further tests are needed.

If at step 987, the decision is that no more tests are needed, the results of all the tests are output for the use by the user or the subject or both. The flow described hitherto with reference to FIG. 9 shows one of the advantages of the disclosed apparatus and the disclosed method that during one visit or one sitting with the patient all the tests deemed necessary by the user, that is, an operator, an optometrist or an ophthalmologist, may be conducted.

Thus, the disclosed apparatus and method may have the following advantages. Various tests of the subject's vision may be conducted in a single sitting and setup of the disclosed apparatus. If the subject has refraction errors, they may be determined. With the same setup the errors in vision of the subject may be compensated for, before conducting the other tests of the subject's vision, using a tunable lens. Since the disclosed apparatus is head mounted, the need for large space for setting up various testing facilities apparatuses may be eliminated. Various operations of the apparatus are controlled by its computational device which reduces human intervention and probability of errors.

While specific language has been used to describe the disclosure, any limitations arising on account of the same are not intended. As would be apparent to a person skilled in the art, various working modifications may be made to the method in order to implement the inventive concept as taught herein.

The figures and the foregoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein. Moreover, the actions of any flow diagram need not be implemented in the order shown, nor do all of the acts necessarily need to be performed. Also, those acts that are not dependent on other acts may be performed in parallel with the other acts. The scope of embodiments is by no means limited by these specific examples. Numerous variations, whether explicitly given in the specification or not, such as differences in structure, dimension, and use of material, are possible. The scope of embodiments is at least as broad as given by the following claims.

We claim:

1. An apparatus for conducting one or more tests of a subject's vision, the apparatus configured for being worn by a subject, and the apparatus comprising:
- a display device for displaying a visual stimulus;
- a feedback unit for receiving a response of the subject to the visual stimulus and conveying the response to a computational device;
- a tunable lens; and
- a retractable periscopic arm arrangement comprising mirrors configured to enable visual observation of the subject's eyes by an operator during a setup phase, for observing an inter-pupillary distance of the subject's eyes and for co-axially aligning a position of the tunable lens with the subject's eyes, the retractable periscopic arm arrangement being movable between a deployed position for the visual observation during the setup phase and a retracted position during vision testing, wherein the computational device is configured for:
- controlling the display device for displaying the visual stimulus to the subject for the subject to view through the tunable lens;
- determining one or more characteristics of the vision of the subject based on the subject's response conveyed through the feedback unit;
- tuning characteristics of the tunable lens based on the determined one or more characteristics of the vision of the subject; and
- outputting values of the determined one or more characteristics of the vision of the subject.

2. The apparatus of claim 1, further comprising:
- a proximity sensor communicatively coupled to the computational device; and
- a projector communicatively coupled to the computational device, wherein the computational device is further configured for:
- measuring a distance between the subject and a passive screen in front of the subject and distant from the subject, based on an output of the proximity sensor; and
- controlling the projector for projecting the visual stimulus on the passive screen, wherein a size of the visual stimulus projected is proportional to the measured distance between the subject and the passive screen.

3. The apparatus of claim 1, wherein the tunable lens is an electrically tunable lens, the characteristics of which are alterable by applying voltages to electrodes.

4. The apparatus of claim 2, further comprising a light sensor for measuring an ambient light intensity for conveying intensity data to the computational device, wherein the computational device is further configured for controlling brightness of the visual stimulus projected on the passive screen by the projector proportional to the ambient light intensity, brightness of a projected display being appropriate for determining the one or more characteristics of the vision of the subject.

5. The apparatus of claim 2, further comprising a light sensor for measuring a light intensity on the passive screen for conveying intensity data to the computational device, wherein the computational device is further configured for controlling brightness of the visual stimulus projected on the passive screen by the projector proportional to the light intensity on the passive screen, brightness of a projected display being appropriate for determining the one or more characteristics of the vision of the subject.

6. The apparatus of claim 1, wherein the visual stimulus is one or more visual stimuli selected from a group of stimuli comprising stimulus for testing a field of vision, a visual acuity, a contrast sensitivity, a color vision, a binocular function, a visual search, a glare and light/dark adaptation, and a visual efficiency.

7. A method for conducting one or more tests of a subject's vision, wherein a subject is wearing an apparatus configured for being worn by the subject, the method comprising:
- a step of displaying a visual stimulus on a display device of the apparatus, by a computational device of the apparatus, for viewing through a tunable lens of the apparatus, by the subject;
- a step of conveying, to the computational device, the subject's response to the visual stimulus, by a feedback unit of the apparatus, configured for receiving the subject's response to the visual stimulus;

a step of enabling visual observation, by mirrors of a retractable periscopic arm arrangement of the apparatus, of the subject's eyes by an operator during a setup phase, for observing an inter-pupillary distance of the subject's eyes and for co-axially aligning a position of the tunable lens with the subject's eyes, the retractable periscopic arm arrangement being movable between a deployed position for the visual observation during the setup phase and a retracted position during vision testing;

determining, by the computational device, one or more characteristics of the vision of the subject based on the subject's response conveyed through the feedback unit; and a step of outputting values of a refraction error and the determined one or more characteristics of the subject's vision.

8. The method of claim 7, wherein the visual stimulus is one or more visual stimuli selected from a group of stimuli comprising a stimulus for testing field of vision, a visual acuity, a contrast sensitivity, a color vision, a binocular function, a visual search, a glare and light/dark adaptation, and a visual efficiency.

9. The method of claim 7, wherein the visual stimulus for refraction testing includes projecting on a passive screen, located at a distance from the subject and in front of the subject, by a projector of the apparatus, and wherein a size of the visual stimulus is proportional to the distance between the passive screen and the subject.

10. The method of claim 7, further comprising a step of adjusting a brightness of the visual stimulus proportional to an ambient light intensity measured by a light sensor of the apparatus.

* * * * *